US011260268B1

(12) United States Patent
Smyser et al.

(10) Patent No.: US 11,260,268 B1
(45) Date of Patent: Mar. 1, 2022

(54) SYSTEMS, METHODS, AND APPARATUS FOR ISOMETRIC, ISOKINETIC, ISOTONIC, AND ISODYNAMIC EXERCISE

(71) Applicant: MD Systems, Inc., Westerville, OH (US)

(72) Inventors: Michael A. Smyser, New Smyrna Beach, FL (US); David Ferguson, New Albany, OH (US); Ronald L. Wiley, Oxford, OH (US)

(73) Assignee: MD Systems, Inc., Westerville, OH (US)

( * ) Notice: Subject to any disclaimer, the term of this patent is extended or adjusted under 35 U.S.C. 154(b) by 359 days.

(21) Appl. No.: 15/884,655

(22) Filed: Jan. 31, 2018

Related U.S. Application Data

(63) Continuation-in-part of application No. 15/788,735, filed on Oct. 19, 2017, now Pat. No. 10,603,542.
(Continued)

(51) Int. Cl.
*A63B 23/16* (2006.01)
*A63B 71/06* (2006.01)
(Continued)

(52) U.S. Cl.
CPC ............ *A63B 23/16* (2013.01); *A61B 5/1125* (2013.01); *A63B 21/002* (2013.01);
(Continued)

(58) Field of Classification Search
CPC . A61B 5/1125; A63B 21/002; A63B 21/0023; A63B 21/0083; A63B 21/0087;
(Continued)

(56) References Cited

U.S. PATENT DOCUMENTS 4,844,055 A * 7/1989 Rawcliffe .............. A63B 24/00
601/24
4,884,445 A 12/1989 Sadoff et al.
(Continued)

FOREIGN PATENT DOCUMENTS

WO 8702567 A1 5/1987
WO 2004032701 A2 4/2004

OTHER PUBLICATIONS

Choquette, et al., "Blood Pressure Reduction in 'Borderline' Hypertensivies Following Physical Training" Can. Med. Assoc. J. 1108:699-703, 1973.
(Continued)

*Primary Examiner* — Joshua Lee
(74) *Attorney, Agent, or Firm* — Wood Herron & Evans LLP

(57) ABSTRACT

A scientifically controlled exercise based on a measurement of maximum voluntary contraction (MVC). A mechanical apparatus includes a sensor, an actuator, and a processor. The apparatus receives a mechanical exertion from a user while the processor receives signals from the sensor and sends signals to the actuator to control the mechanical apparatus. The processor measures a MVC exerted by a user and determines a protocol for the exercise based on the measured MVC. The protocol includes a specified exertion to be performed by a user, the specified force and velocity profile governing the exertion, and a specified sequence of repetitions of the exertion, spaced by rest periods. The protocol includes real-time feedback to the user related to compliance with the protocol. The methodology and equipment described herein provides users a safe and effective means of improving muscular strength or endurance and ameliorating various neurological or physiological conditions.

32 Claims, 8 Drawing Sheets

Related U.S. Application Data

(60) Provisional application No. 62/410,271, filed on Oct. 19, 2016.

(51) Int. Cl.

| | | |
|---|---|---|
| *A63B 21/008* | (2006.01) | |
| *A63B 24/00* | (2006.01) | |
| *A63B 21/00* | (2006.01) | |
| *A63B 21/002* | (2006.01) | |
| *A61B 5/11* | (2006.01) | |

(52) U.S. Cl.
CPC ...... *A63B 21/0023* (2013.01); *A63B 21/0083* (2013.01); *A63B 21/0087* (2013.01); *A63B 21/4035* (2015.10); *A63B 24/0062* (2013.01); *A63B 24/0087* (2013.01); *A63B 71/0622* (2013.01); *A63B 2024/0093* (2013.01); *A63B 2220/20* (2013.01); *A63B 2220/51* (2013.01); *A63B 2225/09* (2013.01)

(58) Field of Classification Search
CPC . A63B 21/4035; A63B 23/16; A63B 24/0062; A63B 24/0087; A63B 24/2024; A63B 24/0093; A63B 71/0622; A63B 2220/20; A63B 71/51; A63B 2225/09
See application file for complete search history.

(56) References Cited

U.S. PATENT DOCUMENTS

| | | | | |
|---|---|---|---|---|
| 4,949,729 | A | 8/1990 | Haski | |
| 5,398,696 | A * | 3/1995 | Wiley | A61B 5/225 600/587 |
| 5,904,639 | A * | 5/1999 | Smyser | A61B 5/225 482/1 |
| 6,026,684 | A | 2/2000 | Calder | |
| 6,217,504 | B1 | 4/2001 | Phillips | |
| 6,358,187 | B1 | 3/2002 | Smith | |
| 6,962,569 | B2 * | 11/2005 | Smyser | A61B 5/225 600/595 |
| 7,448,265 | B2 * | 11/2008 | Smyser | A61B 5/225 73/379.02 |
| 2005/0101461 | A1 | 5/2005 | Johnson | |
| 2007/0087913 | A1 * | 4/2007 | Jaquish | A63B 24/00 482/91 |
| 2008/0132388 | A1 * | 6/2008 | Clem | A63B 21/0004 482/91 |
| 2008/0248926 | A1 * | 10/2008 | Cole | A63B 24/00 482/5 |
| 2011/0105962 | A1 * | 5/2011 | Ochi | A61B 5/0488 601/5 |
| 2014/0287876 | A1 * | 9/2014 | Etter | A63B 24/0087 482/5 |
| 2014/0336947 | A1 * | 11/2014 | Walke | A61B 90/98 702/19 |
| 2015/0297128 | A1 * | 10/2015 | Shield | A61B 5/224 600/595 |
| 2016/0059077 | A1 * | 3/2016 | Paul | A63B 71/0622 482/4 |
| 2017/0311866 | A1 * | 11/2017 | Fuss | A61B 5/0488 |
| 2017/0361165 | A1 * | 12/2017 | Miller | A63B 21/00178 |
| 2018/0001181 | A1 * | 1/2018 | von Prellwitz | A63B 71/0622 |
| 2018/0177447 | A1 * | 6/2018 | Herrala | G16H 20/30 |

OTHER PUBLICATIONS

Chrysant et al., Hemodynamic Effects of Isometric Exercise in Normotensive Hypertensive Subjects: Hypertension, Angiology 1978; 29(5):379-85.

Clarke et al., The duration of sustained contractions of the human forearm at different muscle temperatures, J. Physiol., 1958; 143:454-473.

Gilders, et al., "Endurance Training and Blood Pressure in Normotensive and Hypertensive Adults", Med. Sci. Sports Exerc. 21:629-636, 1989.

Hanson P., et al., "Isometric Exercise: Cardiovascular Responses in Normal and Cardiac Populations", Cardiology Clinics 1987;5(2):157-70.

Harris, et al., "Physiological Response to Circuit Weight Training in Borderline Hypertensive Subjects", Med. Sci. Sports Exerc., 19:246-252, 1987.

Howden et al., The effects of isometric exercise training on resting blood pressure and orthostatic tolerance in humans, Exp. Physiol. 2002; 87.4, pp. 507-515.

Hurley, et al., "Resistive Training Can Induce Coronary Risk Factors Without Altering VO.sub.2 max or Percent Body Fat", Med. Sci. Sports Exerc 20:150-154, 1988.

Kiveloff et al., Brief Maximal Isometric Exercise in Hypertension, J. Am Geriatr. Socl. 9:1006-12.

Lind, Editorial: Cardiovascular Responses to Static Exercise (Isometrics, Anyone?), Circulation 1970; 41(2):173-76.

Mathiowetz, et al., "Effect of Elbow Position on Grip and Key Pinch Strength", The Journal of Hand Surgery 10A:694-7, 1985.

Mathiowetz, et al., "Grip and Pinch Strength: Normative Data for Adults", Arch Phys Med Rehabilitation 66:69-72, 1985.

Mathiowetz, et al., "Grip and Pinch Strength: Norms for 6 to 19 Year Olds", The American Journal of Occupational Therapy 40:705-11, 1986.

Mathiowetz, et al., "Reliability and Validity of Grip and Pinch Strength Evaluations", The Journal of Hand Surgery 9A:22-6, 1984.

Mcgowan et al., Isometric Handgrip Training Improves Endothelial Function in Persons Medicated for Hypertension, Experimental & Clinical Cardiology. 2004; 9(1): 68.

Meredith et al., Exercise Training Lowers Resting Renal But Not Cardiac Sympathetic Activity in Human, Hypertension 1991; 18:575-82.

Mitchell, et al., Static (Isometric) Exercise and the Heart: Physiological and Clinical Considerations, Ann Rev Med 1974;25:369-81.

Preston, A Bissell Healthcare Company, JAMAR.RTM. Hydraulic Hand Dynamometer, Owner's Manual, Copyright 1992.

Sammons Preston, Evaluation: JAMAR.RTM. Hydraulic Hand Dynamometer, Product Advertisement, No date.

Seals, et al., "The Effect of Exercise Training on Human Hypertension: A Review", Med. Sci. Sports Exerc., 16:207-215, 1984.

Vecht, R. J. Grahm GWS, Sever PS. "Plasma Noradrenaline Concentrations During Isometric Exercise." Brit Heart J. 1978;40:1216-20.

Visocchi et al., The effect of isometric arm and leg exercise on resting blood pressure and arterial distensibility in person medicated for hypertension, APS Intersociety meeting: Integrative Biology of Exercise—Abstracts, American College ofCardiology Conference, Austin 2004.

Wiley, et al., "Isometric Exercise Training Lowers Resting Blood Pressure", Med. Sci. Sports Exerc. 29:749-754, 1992.

\* cited by examiner

SYSTEMS, METHODS, AND APPARATUS FOR ISOMETRIC, ISOKINETIC, ISOTONIC, AND ISODYNAMIC EXERCISE

RELATED APPLICATIONS

This application is a divisional-in-part of U.S. Ser. No. 15/788,735 filed Oct. 19, 2017, which is a U.S. non-provisional application claiming priority to provisional application U.S. Ser. No. 62/410,271 filed Oct. 19, 2016, both of which are incorporated herein in their entirety.

FIELD OF THE INVENTION

This disclosure generally relates to exercise equipment and methods particular to exercise equipment that control a force and/or velocity profile of an exercise appropriate to each user.

BACKGROUND OF THE INVENTION

Certain forms of exercise are produced by various exercise machines, but some exercise forms are more common than others. For example, an isometric exercise is characterized by a specified force profile with zero fixed velocity, and is commonly provided by various machines which provide a fix load or resistance against muscular movement. Other forms of exercise are also known, but less commonly provided by machines. For example, an isokinetic exercise refers to an exercise characterized by a fixed non-zero velocity with constant or variable force, an isotonic exercise refers to an exercise characterized by a constant force with constant or variable non-zero velocity, and an isodynamic exercise refers to an exercise characterized by an isokinetic or isotonic exercise combined with an isometric exercise. These forms of exercise are often not easily accomplished by existing exercise machines because the user may have difficulty controlling velocity to a constant or zero value.

Various forms of exercise have been studied and shown to provide health benefits in muscular strengthening and endurance while modulating levels of nitric oxide (NO) and its synthesis in the cardiovascular system, and enlisting changes in the sympathetic/parasympathetic nervous system to modify heart rate and stroke volume yielding multiple benefits to users within a variety of disease states. Exercise modalities can provide a means of stressing the cardiovascular system in a way that modulates NO levels by applying pressure on the endothelial cells lining the vessels invoking multiple outcomes beneficial to the user. The modulation of NO levels is part of a feedback system that responds in part to the stretching and extensibility of blood vessels of the body. As such, certain forms of exercise are known to play a role in regulating NO release, and effectively providing some of the benefits of statin drugs, including improvement in endothelial function, increased NO bioavailability, anti-oxidant effects, anti-inflammatory protection, and stabilization of atherosclerotic plaques. In addition to the effects of the modulation of NO bioavailability, exercise is also known to modulate blood cholesterol and blood lipid composition.

Despite the noted health benefits of various forms of exercise, isometric, isokinetic, isotonic, and/or isodynamic exercises are not widely practiced due in part to the lack of suitable exercise equipment to control the exercise, particularly so that it may be safely performed.

SUMMARY OF THE INVENTION

The disclosed embodiments fulfill a need by providing systems, methods, and computer program products that enable isometric, isokinetic, isotonic, and/or isodynamic large muscle group exercises to be performed according to a user-specific protocol that includes specified exertions to be performed by a user, a specified force and velocity profile governing the exertion, the length of the exertion and rest periods, and a specified sequence of repetitions and rest periods. The exercise protocols are tailored to each specific user's needs by measuring the large muscle group strength to be exercised and therefore provide enhanced health benefits over conventional exercise systems and programs in which the average user elects to perform without proper guidance.

According to an embodiment, a processor based method of performing exercise is disclosed. The method includes using a processor to measure a maximum voluntary contraction (MVC) exerted by a large muscle group of a user and to determine a protocol for the exercise based on the measured MVC. The protocol may include a specified exertion to be performed by a user, duration of the exertion, a specified force and velocity profile governing the exertion, and a specified sequence of repetitions of the exertion, as well as specified rest periods. The method may further include prompting the user to perform the exercise according to the determined protocol and constraining the user to perform the exercise according to the force and/or velocity profile. The method may further include measuring force and/or velocity data associated with the exercise performed by the user and providing feedback to the user regarding the measured force and/or velocity data while the user is performing the exercise to control the exercise, and scoring user compliance with the specific regimen.

According to a further embodiment, a system for performing exercise is disclosed. The system includes a mechanical apparatus that receives a mechanical exertion from a user, a sensor, an actuator, and a processor. The mechanical apparatus that receives a mechanical exertion from a user constrains the resulting force and/or displacement of the mechanical apparatus according to a specified force and velocity profile. The sensor measures force and displacement of the mechanical apparatus resulting from the exertion from the user and generates a signal that is provided to the processor. The actuator controls the displacement of the mechanical apparatus in response to the exertion from the user and in response to signals received from the processor. The processor receives signals from the sensor and sends signals to the actuator to control the actuator based on the specified force and velocity profile in response to signals generated by the sensor.

The processor measures a maximum voluntary contraction (MVC) exerted by a user based on one or more signals received from one or more sensors in response to the exertion and determines a protocol for the exercise based on the measured MVC. The protocol includes a specified exertion and rest periods to be performed by a user, a specified force and velocity profile governing the exertion, and a specified sequence of repetitions of the exertion, as well as rest periods. The processor may further obtain physical dimensions of the user to compute a range of motion for the protocol, may identify an optimal location for the MVC measurement within that range of motion, or may detect the position where the MVC is measured within the range of motion.

In further embodiments, the processor prompts the user to perform the exercise according to the determined protocol. While the user engages in the specified exercise the processor sends signals to the actuator to constrain the user to perform the exercise according to the force and/or velocity profile. During the exercise the processor measures force and/or velocity data associated with the exercise performed by the user based on signals received from the sensor and provides feedback to the user regarding the measured force and/or velocity data based on signals received from the sensor and measures user compliance with the exercise protocol.

According to a further embodiment, a non-transitory computer readable storage device having computer program instructions stored thereon is disclosed. The computer program instructions specify operations to be performed by a processor. For example, when executed by a processor, the computer program instructions cause the processor to (1) measure a maximum voluntary contraction (MVC) exerted by a user, (2) determine a protocol for the exercise based on the measured MVC, (3) prompt the user to perform the exercise and rest periods according to the determined protocol, (4) constrain the user to perform the exercise and rest periods according to the protocol, (5) measure force and/or velocity data associated with the exercise performed by the user, and (6) provide feedback to the user regarding the measured force and/or velocity data while the user is performing the exercise or resting. Further, the computer program instructions specify operations that cause the processor to determine the exercise protocol, with the protocol including a specified exertion to be performed by a user throughout a specified range of motion, a specified force and velocity profile governing the exertion, and a specified sequence of repetitions of the exertion and rest periods, and instantaneous and/or final compliance scores.

Further embodiments, features, and advantages, as well as the structure and operation of the various embodiments, are described in detail below with reference to the accompanying drawings.

BRIEF DESCRIPTION OF THE DRAWINGS

Embodiments are described with reference to the accompanying drawings. In the drawings, like reference numbers may indicate identical or functionally similar elements.

Figure 1A:
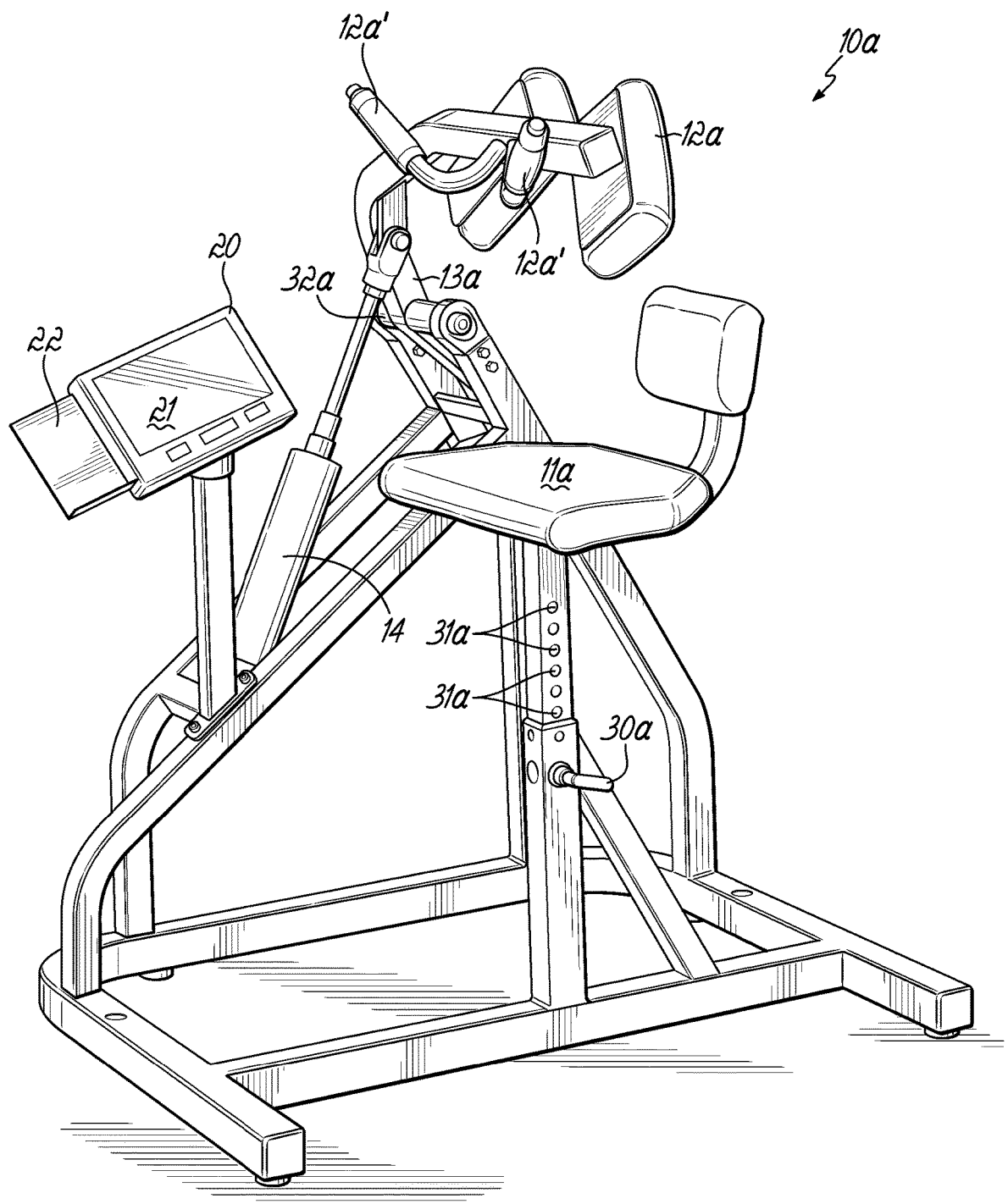
FIG. 1A is a perspective view of an exercise machine for performing an abdominal exercise protocol in accordance with one embodiment of principles of the present invention.

The disclosed invention is described below with reference to the accompanying drawings. In the drawings, like reference numbers generally indicate identical, functionally similar, and/or structurally similar elements. The drawing in which an element first appears is indicated by the leftmost digit(s) in the reference number.

DETAILED DESCRIPTION

This disclosure provides systems, methods, and computer program products for performing exercise in which a force and displacement of a mechanical apparatus, resulting from a mechanical exertion imposed by a user performing the exercise, is constrained according to a specified force and/or velocity profile. As such, disclosed systems and methods allow a user to properly perform one or more of isometric (specified force/zero velocity), isokinetic (fixed velocity/constant or variable force), isotonic (constant force/non-zero velocity), and isodynamic (isokinetic or isotonic with isometric) exercises according to a protocol specifically designed for the user based on a measured maximum voluntary contraction (MVC) associated with the user.

References in this specification to "one embodiment," "an embodiment," an "example embodiment," etc., indicate that the embodiment described may include a particular feature, structure, or characteristic, but not every embodiment may necessarily include the particular feature, structure, or characteristic. Moreover, such phrases are not necessarily referring to the same embodiment. Further, when a particular feature, structure, or characteristic may be described in connection with an embodiment, it may be submitted that it may be within the knowledge of one of ordinary skill in the relevant art to affect such feature, structure, or characteristic in connection with other embodiments whether or not explicitly described.

The following detailed description refers to the accompanying drawings that illustrate exemplary embodiments. Other embodiments are possible, and modifications may be made to the embodiments within the spirit and scope of this description. Those of ordinary skill in the relevant art with access to the teachings provided herein will recognize additional modifications, applications, and embodiments within the scope thereof and additional fields in which embodiments would be of significant utility. Therefore, the detailed description is not meant to limit the embodiments described below.

Embodiments of the invention may be implemented in hardware, firmware, software, or any combination thereof. Embodiments may also be implemented as instructions, written or otherwise, stored on a non-transitory machine-readable medium, which may be read and executed by one or more processors or a user in conjunction with exercise equipment. A machine-readable medium may include any mechanism for storing or transmitting information in a form readable by a machine (e.g., a computing device). For example, a machine-readable medium may include read only memory (ROM); random access memory (RAM); magnetic disk storage media; optical storage media; flash memory devices; electrical optical, acoustical or other forms of propagated signals (e.g., carrier waves, infrared signals, digital signals, etc.), and others. Further firmware, software routines, and instructions may be described herein as performing certain actions. However, it should be appreciated that such descriptions are merely for convenience and that such actions in fact result from computing devices, processors, controllers, or other devices executing the firmware, software, routines, instructions, etc.

Systems of the disclosed invention may be implemented as extensions of conventional exercise equipment. Conventional systems provide a mechanical apparatus that imposes a resistance force in response to an exertion imposed by a user on the mechanical apparatus. The mechanical apparatus further constrains the motion that results from the exertion imposed by the user on the mechanical apparatus. Examples of conventional exercise equipment include: a leg press, a leg extension machine, a leg curl machine, a standing hip machine, an abdominal machine, a lower back machine, an upper back machine, a lateral pull down machine, a military press machine, a triceps machine, an arm curl machine, a seated butterfly machine, a seated calf machine, a lateral shoulder raise machine, a squat machine, and a hip abductor machine, as would readily be appreciated by persons of ordinary skill in the art.

Conventional systems such as those mentioned above do not provide for a user-specific exercise protocol in which various exercise modalities (e.g., isometric, isotonic, isokinetic, and isodynamic) may be selected. In contrast, the disclosed embodiments provide sensors and actuators that control the force and velocity profile of the mechanical apparatus in response to an exertion imposed by a user. In certain embodiments, the force/velocity profile is tailored to an individual user based on a measured MVC for the user.

Turning now to specific examples, devices for performing exercises in accordance with principles of the present invention are illustrated in FIGS. 1A-1D. Each is microprocessor driven and includes sensors and actuators for the purpose of performing controlled protocol exercises, and may be programmed to carry out various exercise protocols.

FIG. 1A illustrates an abdominal exercise machine 10a in accordance with principles of the present invention. The machine includes a seat 11a for the user to mount the machine, and a chest pad 12a for the user to apply force using abdominal muscles. The user also grips handlebars 12a' to stabilize the user's chest against the machine during operation. The range of motion of the chest pad 12a is controlled by a rotating arm 13a rotationally hinged on an axle 32a to the machine frame. The motion of arm 13a is controlled by an actuator 14 which provides a linear force to the arm (toward and/or away from the user's chest), and produces measurements of force applied by the user and velocity as driven by control of actuator 14. Control of actuator 14 is accomplished by a display unit 20, which has internal circuitry for controlling actuator 14 and further incorporates a display 21 for displaying information to the user. Display 21 further includes a touch screen function to allow user input of information and control of the apparatus. A supporting shelf 22 for a mobile electronic device (smartphone, PDA, tablet, etc.) is integrated into the housing of the display unit 20 to allow a user to conveniently store a mobile device while using the machine. As noted below the machine electronics may also communicate with the mobile device before, after or during use. The machine is adjustable for the user's height via an adjustment peg 30a which can be placed in one of a plurality of locations 31a to appropriately adjust for the user's height.

Figure 1B:
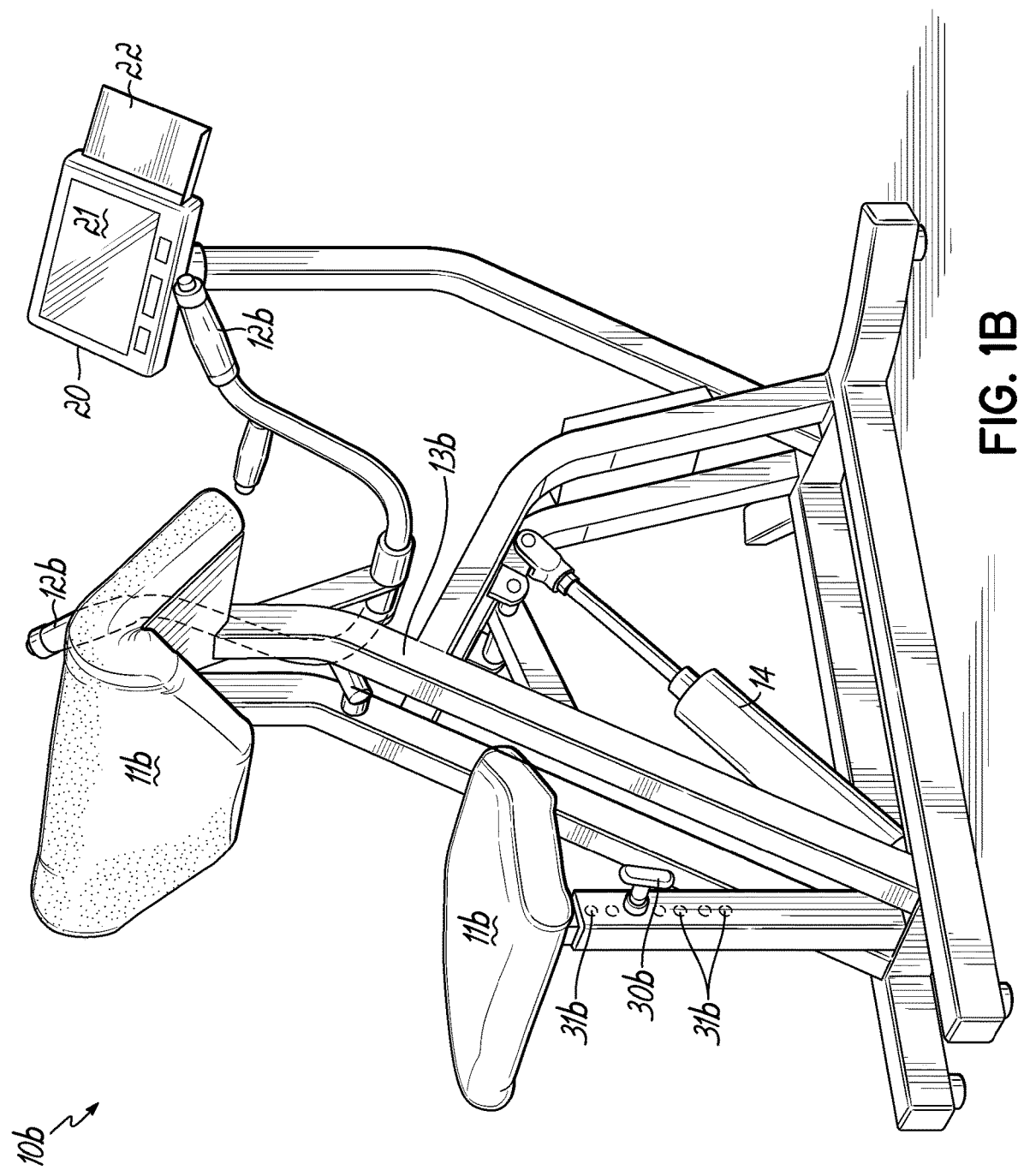
FIG. 1B is a perspective view of an exercise machine for performing an arm curl (bicep/tricep/wrist and finger) exercise protocol in accordance with one embodiment of principles of the present invention.

FIG. 1B illustrates an arm curl exercise machine 10b in accordance with principles of the present invention. The machine includes a seat and chest rest 11b for the user to mount the machine, and a handlebar 12b for the user to grasp (using one of two available sets of handles) to apply force using bicep and/or tricep and wrist and finger muscles. The range of motion of the handlebar 12b is controlled by a rotating arm 13b rotationally hinged to the machine frame. The motion of arm 13b is further coupled to an actuator 14 which provides a linear force to the arm (torque toward and/or away from the user's chest resisting arm curl), and produces measurements of force and velocity. Control of actuator 14 is accomplished by a display unit 20, which has internal circuitry for controlling actuator 14 and further incorporates a display 21 for displaying information to the user. Display 21 further includes a touch screen function to allow user input of information and control of the apparatus, and a supporting shelf 22 for a mobile electronic device as in the machine of FIG. 1A. The machine is adjustable for the user's height via an adjustment peg 30b which can be placed in one of a plurality of locations 31b to appropriately adjust for the user's height.

Figure 1C:
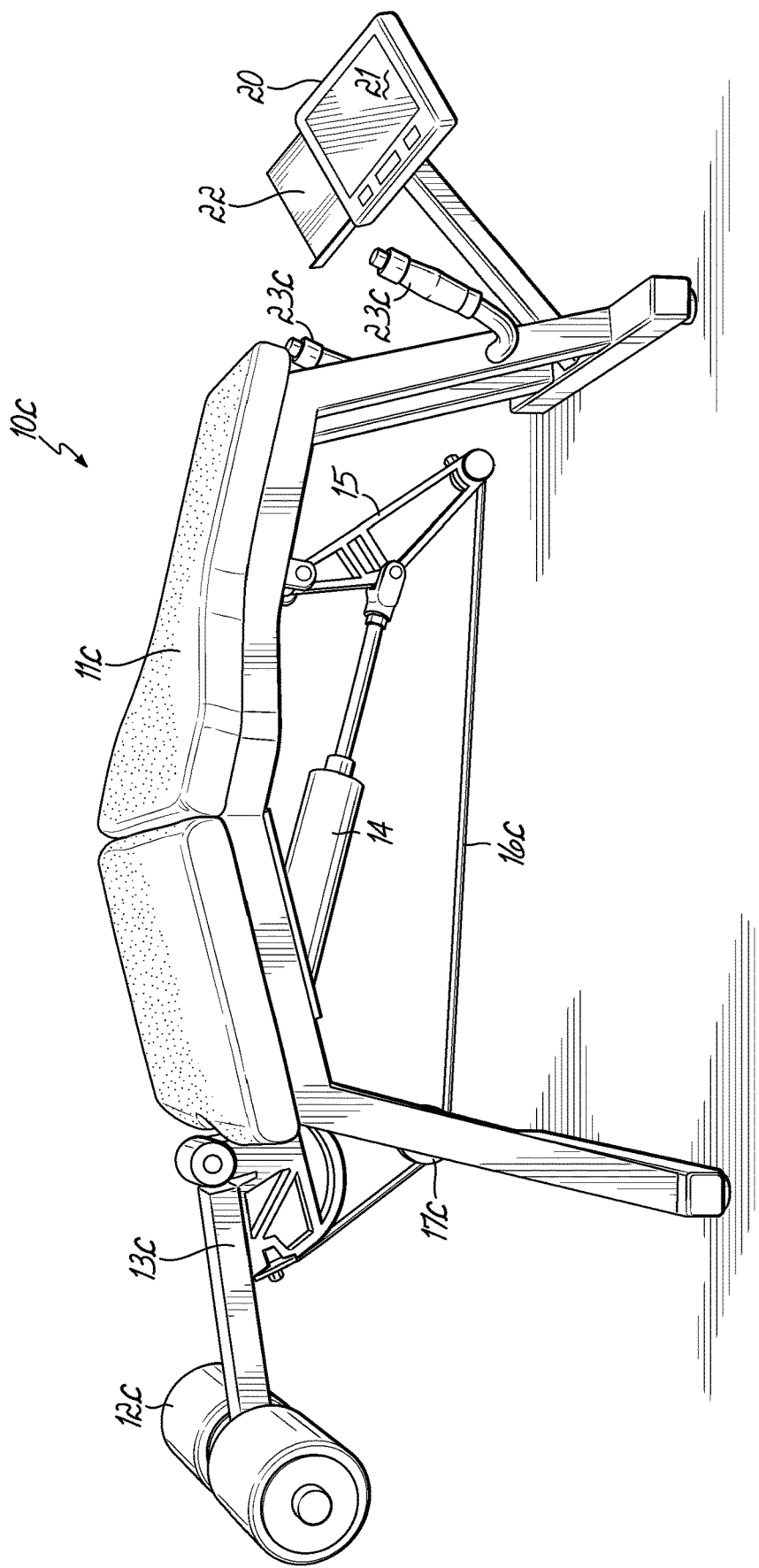
FIG. 1C is a perspective view of an exercise machine for performing a leg curl exercise protocol in accordance with one embodiment of principles of the present invention.

FIG. 1C illustrates a leg curl exercise machine 10a in accordance with principles of the present invention. The machine includes a table 11c for the user to mount the machine, and a lower leg pad 12c. The user positions his or her lower legs under the leg pad 12c and applies force thereto using hamstring muscles of the user's legs. The user may also grasp handgrips 23c to stabilize the user's body on the table 11c during the exercise. The range of motion of the leg pad 12c is controlled by a rotating arm 13c rotationally hinged to the machine frame. The motion of arm 13c is controlled by an actuator 14 which is coupled to a control arm 15 which is connected via a tension element, such as a cable 16c and pulley 17c to arm 13c. Actuator 14 provides a linear force in compression to the arm 15 which is conveyed via cable 16c, resisting movement of arm 13c against the hamstring muscles of the user. Actuator 14 further provides a sufficient linear force in extension to take up slack in the cable 16c when the user releases the arm 13c to the rest position shown in FIG. 1C. Actuator 14 also produces measurements of force and velocity. Control of actuator 14 is accomplished by a display unit 20, which has internal circuitry for controlling actuator 14 and further incorporates a display 21 for displaying information to the user, as well as a supporting shelf 22 for a mobile electronic device. Display 21 further includes a touch screen function to allow user input of information and control of the apparatus.

Figure 1D:
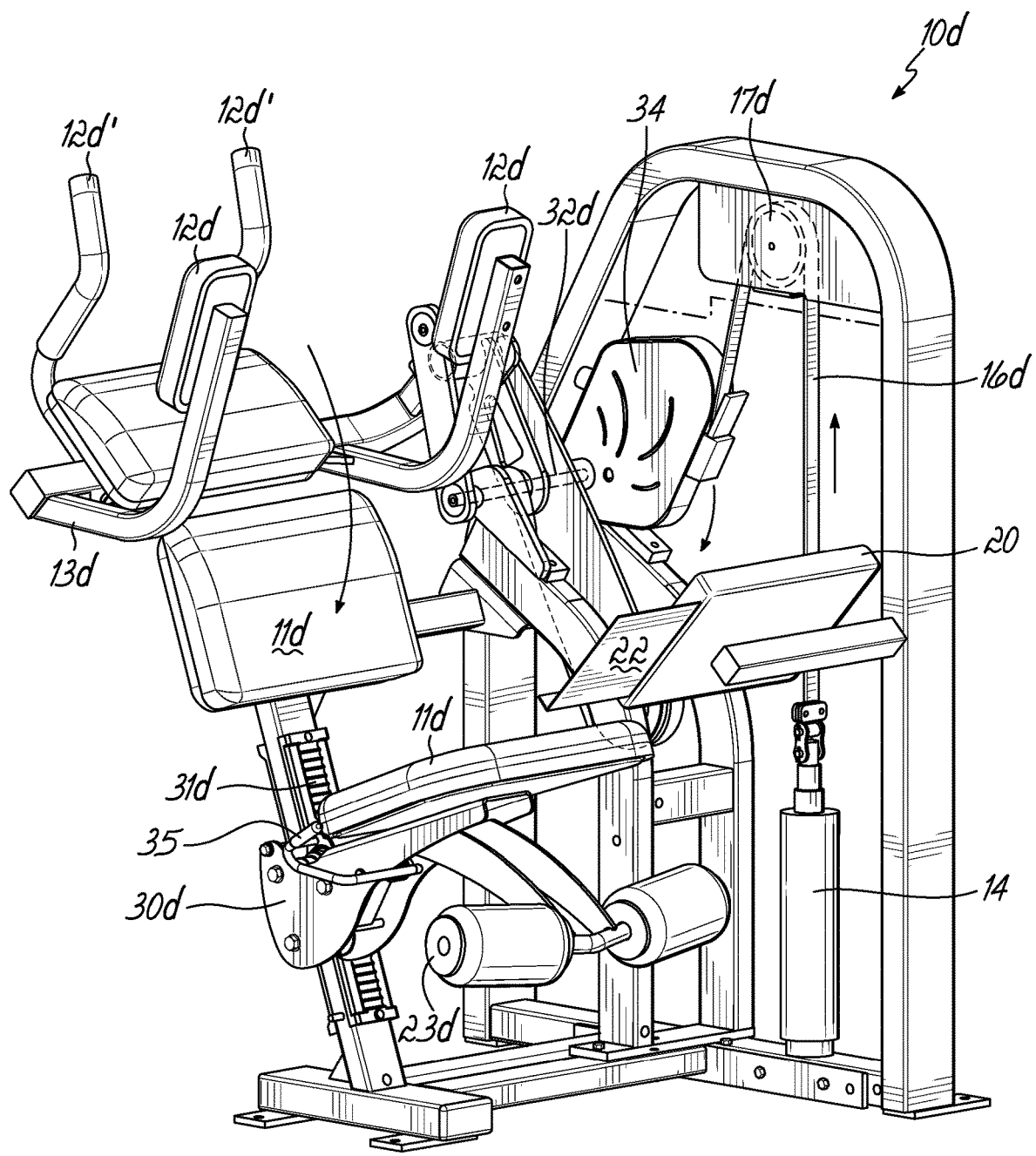
FIG. 1D is a perspective view of an exercise machine for performing an abdominal exercise protocol in accordance with another embodiment of principles of the present invention.

FIG. 1D illustrates an alternative abdominal exercise machine 10d in accordance with principles of the present invention. The machine includes a seat 11d for the user to mount the machine and forearm pads 12d and handlebars 12d', for the user to grasp or press to apply force to the machine using tricep and abdominal muscles. The user also hooks the user's ankles behind pads 23d to stabilize the user's body in the seat 11d during exercise with the machine. The machine includes both pads 12d and handlebars 12d' but in a typical use case only one of these would be used to apply force during operation. The forearm pads 12d and handlebars 12d' are connected to a rotatable structure 13d, which is rotationally hinged on an axle 32d to the machine frame. The motion of structure 13d is transmitted through a transmission 34 to a belt 16d which (via pulley 17d) applies linear force to an actuator 14. Actuator 14 which provides a linear force in extension which is conveyed via tension element, such as a belt 16*d*, resisting movement of structure 13*d* against the tricep and abdominal muscles of the user. Actuator 14 further provides a sufficient linear force in compression to take up slack in the belt 16*d* when the user releases the structure 13*d* to the rest position shown in FIG. 1D. Actuator further produces measurements of force applied by the user and velocity as driven by control of actuator 14. Control of actuator 14 is accomplished by a display unit 20 which incorporates a display 21 for displaying information to the user. Display 21 further includes a touch screen function to allow user input of information and control of the apparatus, and a supporting shelf 22 for a mobile electronic device. The machine is adjustable for the user's height via an adjustable slider 30*d* with an integral pawl that engages or releases teeth 31*d* in a track in response to a control lever 35.

The embodiments described above with reference to FIGS. 1A-1D provide a few illustrative examples in which principles of the disclosed invention may be employed. These examples, however, are not limiting and many more examples would be readily apparent to persons of ordinary skill in the art. Such further examples are therefore within the scope of the disclosed invention as defined by the claims presented below.

Figure 2:
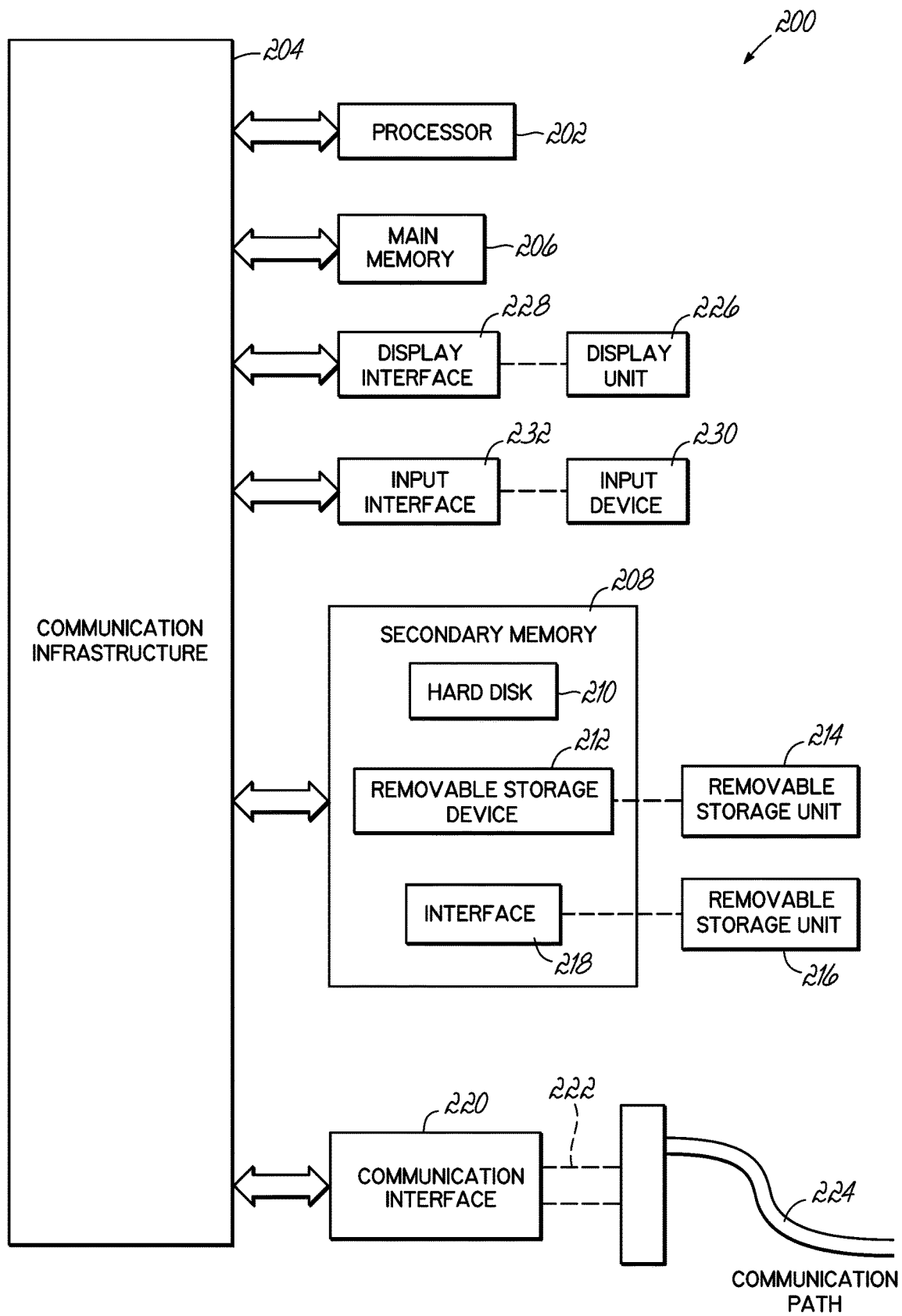
FIG. 2 is a block diagram of an example computer system in which embodiments of the disclosed invention, or portions thereof, may be implemented as computer-readable code, which is executed by one or more processors, according to an embodiment.

FIG. 2 is a block diagram of an example computer system 200 in which embodiments of the disclosed invention, or portions thereof, may be implemented as computer-readable code, which is executed by one or more processors causing the one or more processors to perform operations of the disclosed invention, according to an embodiment.

For example, the embodiments of FIGS. 1A, 1B, 1C and 1D may include components implementing a computer system 200 using hardware, software, firmware, tangible computer readable media having instructions stored thereon, or a combination thereof and may be implemented in one or more computer systems or other processing system.

If programmable logic is used, such logic may be executed on a commercially available processing platform or a special purpose device. One of ordinary skill in the art may appreciate that embodiments of the disclosed subject matter can be practiced with various computer system configurations, including multi-core multiprocessor systems, minicomputers, mainframe computers, computers linked or clustered with distributed functions, as well as pervasive or miniature computers that may be embedded into virtually any device.

Various embodiments of the invention are described in terms of this example computer system 200. After reading this description, it will become apparent to persons of ordinary skill in the relevant art how to implement the invention using other computer systems and/or computer architectures. Although operations may be described as a sequential process, some of the operations may in fact be performed in parallel, concurrently, and/or in a distributed environment, and with program code stored locally or remotely for access by single or multiprocessor machines. In addition, in some embodiments the order of operations may be rearranged without departing from the spirit of the disclosed subject matter.

As will be appreciated by persons of ordinary skill in the relevant art, a computing device for implementing the disclosed invention has at least one processor, such as processor 202, wherein the processor may be a single processor, a plurality of processors, a processor in a multi-core/multi-processor system, such system operating alone, or in a cluster of computing devices operating in a cluster or server farm. Processor 202 may be connected to a communication infrastructure 204, for example, a bus, message queue, network, or multi-core message-passing scheme.

Computer system 200 may also include a main memory 206, for example, random access memory (RAM), and may also include a secondary memory 208. Secondary memory 208 may include, for example, a hard disk drive 210, removable storage device 212 for receiving compatible removable storage units 214, and an interface 218 (USB, USB2 or USB3, Firewire, etc.) for connection to other removable storage units 216 (e.g., thumb drives, portable hard drives, etc.). Removable storage device 212 may include a CD drive, DVD drive, Bluray drive, floppy disk drive, a magnetic tape drive, an optical disk drive, a flash memory, or the like. The removable storage device 212 may be configured to read and/or write data to a removable storage unit 214 in a well-known manner. Removable storage unit 214 may include a floppy disk, magnetic tape, CD, DVD, Bluray or other optical disk, etc., which is read, and written to, by removable storage drive 212. As will be appreciated by persons of ordinary skill in the relevant art, removable storage unit 214 may include a computer readable storage medium having computer software (i.e., computer program instructions) and/or data stored thereon.

In alternative implementations, secondary memory 208 may include other similar devices for allowing computer programs or other instructions to be loaded into computer system 200. Such devices may include, for example, a removable storage unit 216 connectible to system 200 via an interface 218. Examples of such devices may include a program cartridge and cartridge interface (such as that found in video game devices), a removable memory chip (such as EPROM or PROM) and associated socket, USB, USB2, USB3, Firewire sockets, and other removable storage units 216 and interfaces 218 which allow software and data to be transferred to or from the removable storage unit 216 from or to computer system 200.

Computer system 200 may also include a communications interface 220. Communications interface 220 allows software and data to be transferred between computer system 200 and external devices. Communications interfaces 220 may include a modem, a network interface (such as an Ethernet card), a communications port, a PCMCIA slot and card, or the like. Transmission of data between the system and an external device may also be performed using Bluetooth™, Wi-Fi, Zigbee, infrared, digitized audio, or via other communication protocols as would be readily apparent to persons of ordinary skill in the art. According to an embodiment, the system may be further configured or programmed to enable remote, real-time monitoring of exercise parameters. The system may further enable an application (App) to enable two-way communication between the system and an external device to allow remote, real-time setting of exercise protocols or other control functions. Among other functions the App may allow storage and retrieval of machine setup or exercise protocol parameters so that a user may more quickly configure the machine at the beginning of an exercise using data stored in a personal mobile device, and may capture configurations made during an exercise into the personal mobile device prior to departure. In additional embodiments the App could be further embedded into the machine control system including allowing the mobile device operating system to become part of the feedback loop implemented by the machine, using the mobile device's display as the visual feedback to the user and/or using the mobile device processor to control the actuator.

Software and data transferred via communications interface 220 may be in the form of signals 222, which may be electronic, electromagnetic, optical, visual (e.g., display of QR codes which can be read by a camera), acoustic, or other signals capable of being received by communications interface 220. These signals may be provided to communications interface 220 via a communications path 224.

In this document, the terms "computer program storage medium" and "computer usable storage medium" are used to generally refer to storage media such as removable storage unit 214, removable storage unit 216, and hard disk 210. Computer program storage medium/media and computer usable storage medium/media may also refer to memories, such as main memory 206 and secondary memory 208, which may be semiconductor memories (e.g., DRAMS, etc.).

Computer system 200 may further include a display unit 226 that interacts with communication infrastructure 204 via a display interface 228, such as the display screen 21 illustrated in FIGS. 1A, 1B, 1C and 1D. Computer system 200 may further include a user input device 230 that interacts with communication infrastructure 204 via an input interface 232, which may be a touch screen interface as used on display screen 21 in FIGS. 1A, 1B, 1C and 1D. A user input device 230 may also include a mouse, trackball, or the like, as well as a keyboard, keypad, or other input devices.

Computer programs (also called computer control logic or computer program instructions) are stored in main memory 206 and/or secondary memory 208. Computer programs may also be received via communications interface 220. Such computer programs, when executed, enable computer system 200 to implement embodiments as discussed herein. In particular, the computer programs, when executed, enable processor 202 to implement the steps of the method illustrated by flowchart 1000 of FIG. 7, discussed below. Accordingly, such computer programs represent controllers of the computer system 200.

When an embodiment of the present invention is implemented using software, the software may be stored in a computer program product and loaded into computer system 200 using removable storage drive 212, interface 218, hard disk drive 210, or communications interface 220.

Figure 3:
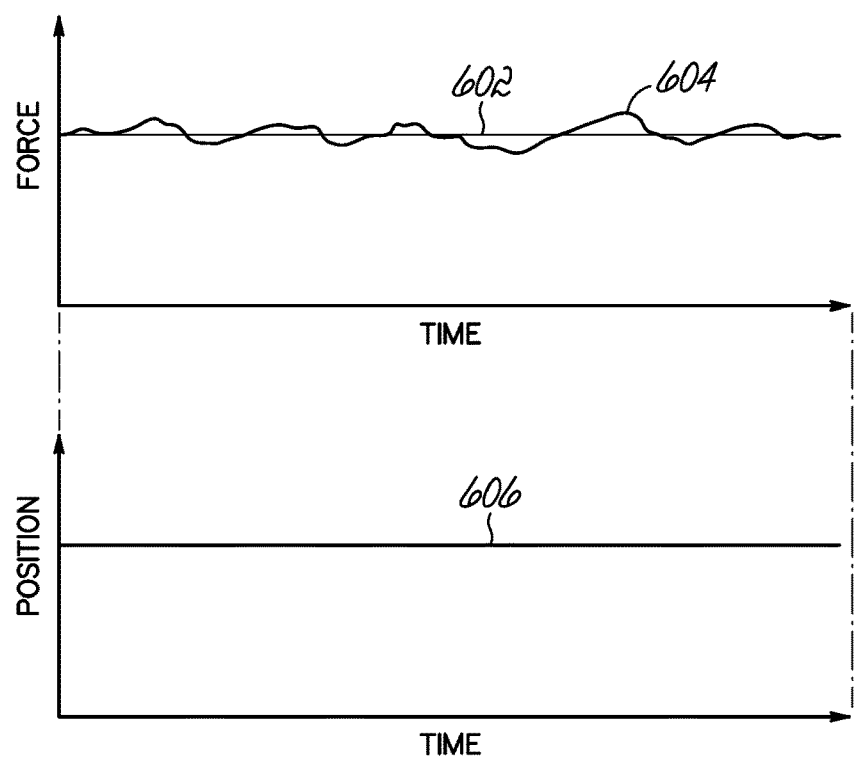
FIG. 3 is a graphical illustration of force and position profiles for an isometric exercise, according to an embodiment.

FIG. 3 is a graphical illustration of force and position profiles for an isometric exercise, according to an embodiment. As mentioned above, an isometric exercise is one in which a user imposes a force on a mechanical apparatus while the position of the mechanical apparatus is held fixed. An exercise protocol for an isometric exercise may include a specified target force 602. In this example, the specified target force 602 is shown as a horizontal line on a force vs. time graph. The target force 602 may be chosen to be a fraction of a user's MVC.

While the user is performing the isometric exercise the user may be prompted to impose the target force 602. A sensor may measure the actual force 604 imposed by the user. In order to perform the exercise according to a specified protocol, a user may attempt to maintain the target force 602. In practice, however, the user's imposed actual force 604 may vary somewhat from the intended target force 602. The mechanical apparatus may be configured to maintain a fixed position 606 vs. time during the isometric exercise.

Figure 4:
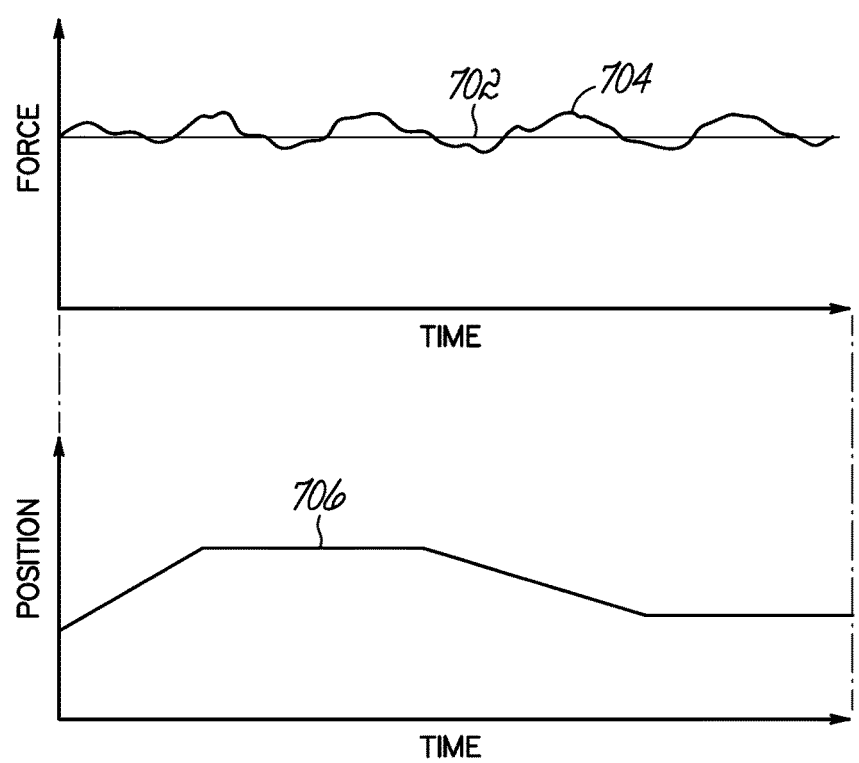
FIG. 4 is a graphical illustration of force and position profiles for an isometric/isotonic exercise, according to an embodiment.

FIG. 4 is a graphical illustration of force and position profiles for an isotonic exercise, according to an embodiment. As mentioned above, an isotonic exercise is one in which a user imposes a constant force on a mechanical apparatus while the mechanical apparatus moves. An exercise protocol for an isotonic exercise may include a specified target force 702. In this example, the specified target force 702 is shown as a horizontal line on a force vs. time graph. The target force 702 may be chosen to be a percentage of a user's MVC. While the user is performing the isotonic exercise the user may be prompted to impose the target force 702. A sensor may measure the actual force 704 imposed by the user. In order to perform the exercise according to a specified protocol, a user may attempt to maintain the target force 702. In practice, however, the user's imposed actual force 704 may vary somewhat from the intended target force 702. In contrast to the isometric example of FIG. 3, in the isotonic exercise example of FIG. 4, the position 706 of the mechanical device varies as a function of time while the exercise is being performed.

Figure 5:
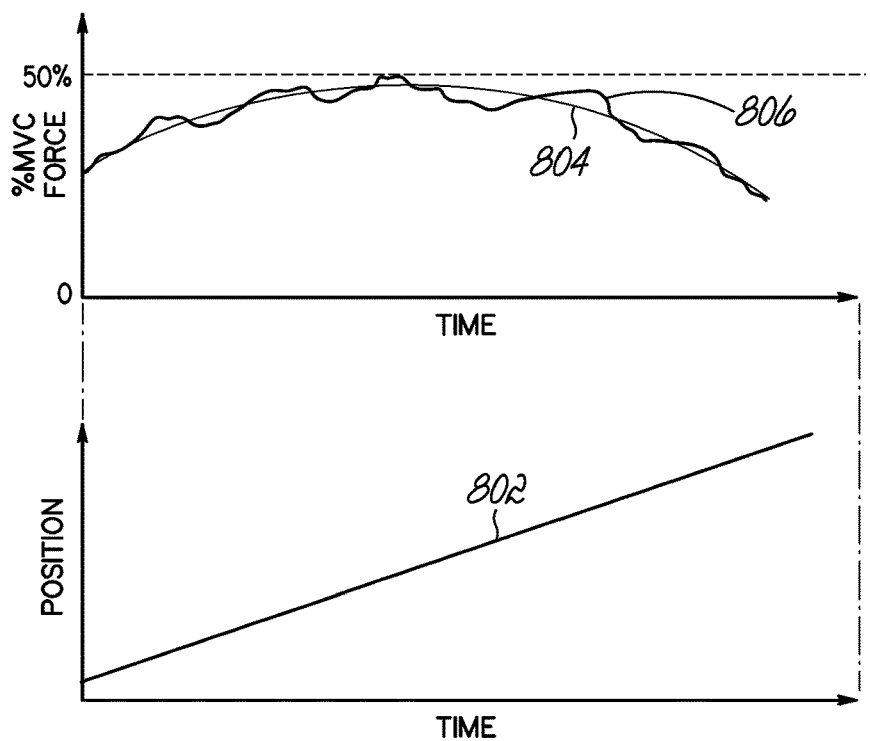
FIG. 5 is a graphical illustration of force and position profiles for an isokinetic exercise, according to an embodiment.

FIG. 5 is a graphical illustration of force and position profiles for an exemplary isokinetic exercise, according to an embodiment. As mentioned above, an isokinetic exercise is one in which the movement of the mechanical apparatus is controlled to have a fixed constant velocity. As illustrated in FIG. 5, a constant velocity corresponds to a sloped straight line (upward or downward) 802 on a position vs. time graph wherein the slope of the line is equal to the constant velocity. A protocol for an isokinetic exercise may specify a force 804 that varies as a function of time, or the specified force 804 may have a constant value, or other types of variable values. In this example, the specified force 804 is illustrated as a percentage of MVC and has a variable value. The curve of force vs. time (and force vs. position since the velocity is constant) may be chosen to track the variation in leverage and/or muscular force vs. position in the musculo-skeletal system for the particular muscle group being exercised, where the force applied is generally greatest at a mid-point in the range of motion and is reduced at the edges of the range of motion. In the illustrated example the peak force in the target curve is 50% of MVC at the optimal location in the range of motion. In further embodiments, the specified force may take on any constant non-zero value. A sensor may measure the actual force 806 imposed by the user. In order to perform the exercise according to a specified protocol, a user may attempt to maintain the target force 804. In practice, however, the user's imposed actual force 806 may vary somewhat from the intended target force 804.

Figure 6:
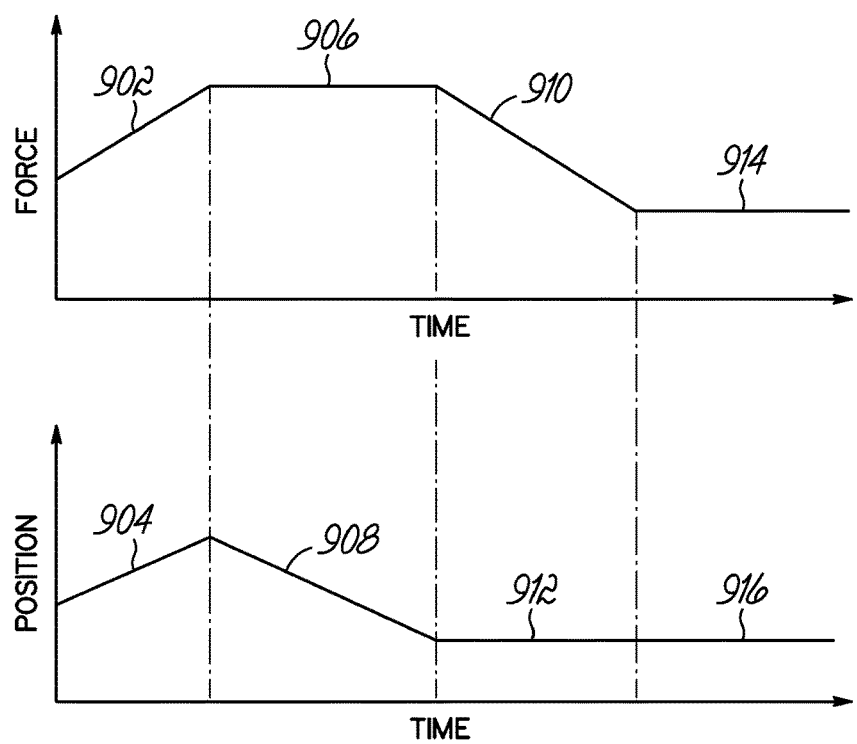
FIG. 6 is a graphical illustration of force and position profiles for an isodynamic exercise, according to an embodiment.

FIG. 6 is a graphical illustration of force and position profiles for an isodynamic exercise, according to an embodiment. As described above, an isodynamic exercise includes combining an isokinetic or isotonic exercise with an isometric exercise. In this example, during a first time interval, the force varies according to a first force vs. time relation 902 while the position changes according to a first position vs. time relation 904. In this example, the position vs. time relation 904 is straight line implying that the mechanical apparatus moves with a constant velocity in a positive direction. Thus, the force 902 and position 904 relations correspond to an isokinetic exercise with variable force in this segment of the exercise.

Further, during a second time interval, the force 906 is held constant while the position 908 varies. For a linear position vs. time relation 908, the force 906 and position 908 relations correspond to an isokinetic exercise where the velocity is negative. For a more general position vs. time relation 908 (i.e., having a non-linear time dependence), the force 906 and position 908 relations correspond to an isokinetic exercise.

During a third time interval, the force 910 varies with time while the position 912 is held constant. Thus, the force 910 and position 912 relations correspond to an isometric exercise (because the position 912 is held constant). In a fourth time interval, both the force 914 and position 916 are held constant. Thus, once again, the force 914 and position 916 relations correspond to an isometric exercise (because the position 912 is held constant).

Figure 7:
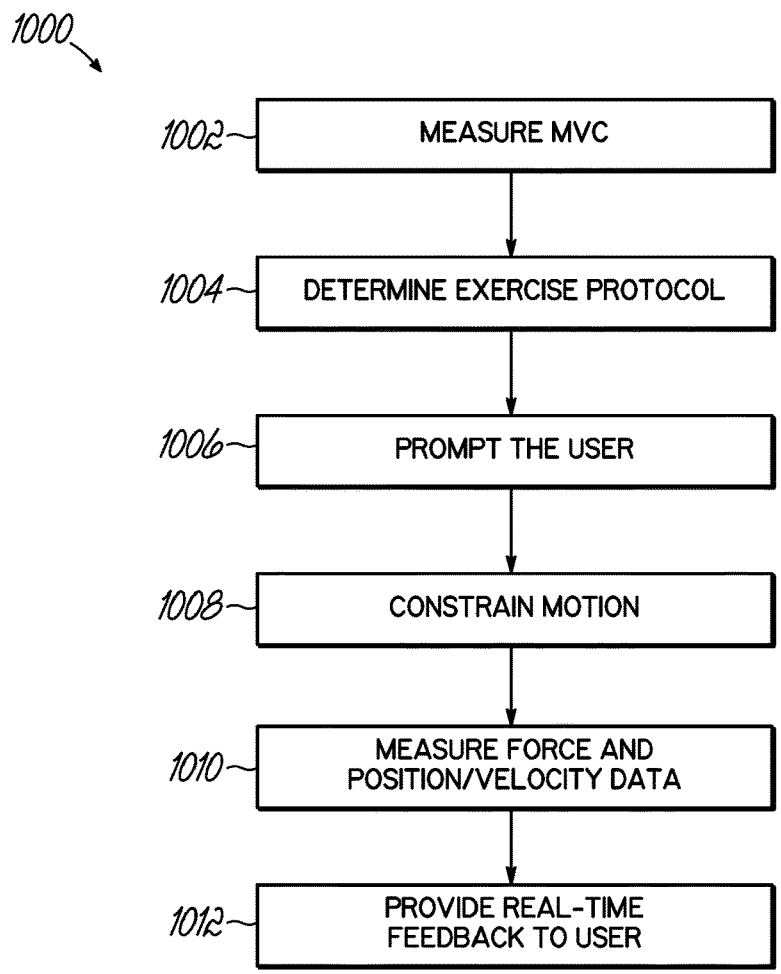
FIG. 7 is a flow chart illustrating a processor based method of performing an exercise by control of an exercise machine such as those of FIGS. 1A-1D, according to an embodiment.

FIG. 7 is a flow chart illustrating a processor based method 1000 of performing exercise, according to an embodiment. In a first step 1002 the method includes measuring a user's MVC. In this regard, a user may be prompted to perform a maximum exertion at a particular position of the machine. For example, if the user is engaging with an apparatus such as the abdominal device of FIG. 1A or 1D, the readout assembly 20 may display a message prompting the user to move to a particular position on seat 11a (generally a partially crouched position, where abdominal muscle force is typically optimized) and then activate the actuator 14 via the touch screen 21, and press against the machine as hard as the user can. The resulting force imposed by the user may then be measured by a sensor incorporated in the actuator 14 and stored in memory by date and time as the MVC, protocol parameters, and final score. Similar processes may be used in the apparatus of FIGS. 1B and 1C.

In a second stage 1004, the method includes determining an exercise protocol based on the measured MVC. The protocol may include a specified exertion to be performed by a user, a specified force and velocity profile governing the exertion, and a specified sequence of repetitions of the exertion. The protocol may specify a force and position vs. time relationship that may be characterized as an isometric, an isokinetic, an isotonic, and/or an isodynamic exercise and a sequence of repetitions of the exertion and spaced by timed rest periods.

According to an embodiment, the force vs. time relation may have a maximum value that is a fraction of the user's measured MVC. The protocol may further specify a time duration of muscle group exertions that is inversely proportional to a predetermined percentage of the user's measured MVC. The protocol may further specify the sequence of repetitions of the exercise to include a specified rest period based on the percentage of MVC selected by the user. In further embodiments, the specified rest period may be characterized by a time duration that is related to a time duration and percentage of MVC of muscle group exertions, or a user selected rest period different from the default proposed by the computer generated protocol.

In further embodiments, the protocol may be determined, in part, by user selections. For example, a display device (e.g., the readout assembly 20 of FIGS. 1A, 1B, 1C and 1D) may display a menu of user-selectable exercise modalities. For example, a user may be prompted to select at least one of an isometric, an isokinetic, an isotonic, and/or an isodynamic exercise.

The protocol may further be determined by a user selection of a fixed regimen or a stepped regimen. For example, in a fixed regimen, the force vs. time and position vs. time relations may have the same form for each of the repetitions of the exertion, spaced with rest periods. In a stepped regimen, for example, the force vs. time and/or the position vs. time profile may change over a plurality of repetitions of the exercise, spaced with rest periods. In a setup operation, the display device may present a menu to the user and request a selection of a fixed or stepped regimen and in stage 1004 the processor may determine the protocol to include a fixed or stepped regimen in accordance with a user input selection.

In a further stage 1006, the user may be prompted to perform the exercise in accordance with the determined protocol exertion for durations measured in seconds. In this regard, the user may be prompted to perform a specified number of repetitions of an exertion. Further, the user may be prompted to exert a predetermined force. In an embodiment, the specified predetermined force may be a percentage of the user's measured MVC. Following exercise efforts, the prompts include rest periods timed in sections and average scores showing compliance (expressed in percentage or otherwise) with the exercise protocol.

In the further stage 1008, the method includes constraining the user to perform the exercise according to the specified force vs. time and position vs. time protocol. Incidentally, the position vs. time protocol can equivalently be specified as a velocity vs. time relation, as would be readily appreciated by persons of ordinary skill in the art. The force vs. time and position/velocity vs. time is constrained using sensors and actuators coupled to the mechanical apparatus to which a user imposes an exertion. For example, sensors measure the position of the mechanical apparatus and the force imposed on the apparatus. Thus, in stage 1010 the method further includes measuring force and position/velocity data.

In a further stage, 1012 the method includes providing feedback to the user regarding the measured force and/or position/velocity data. Feedback may be provided by a visual indicator showing the user a real-time value of the exerted force. Thus, for example, as the user is performing the exercise, the screen 21 on the display device 20 may present a target and an actual value of the user-imposed force having a visual appearance similar to curves 602/604, 702/704, 804/806 of FIGS. 3, 4, and 5, respectively. Similar target and user-imposed forces may be determined and displayed for an isodynamic exercise as seen in FIG. 6, although measured forces have been omitted from FIG. 6 for clarity.

Other feedback may also be provided to the user that informs the user of a degree to which the user complies with the specified exercise protocol. For example, a power exerted by the user may be measured and reported. In this regard, an instantaneous force and velocity may be measured and a power may be determined by multiplying the instantaneous force by the instantaneous velocity to give the instantaneous power. According to an embodiment, the protocol may specify the user to impose the exertion so as to generate a target power. For example, as a force is increased (decreased) the user may decrease (increase) the velocity to maintain a constant power of the exertion.

Figure 8:
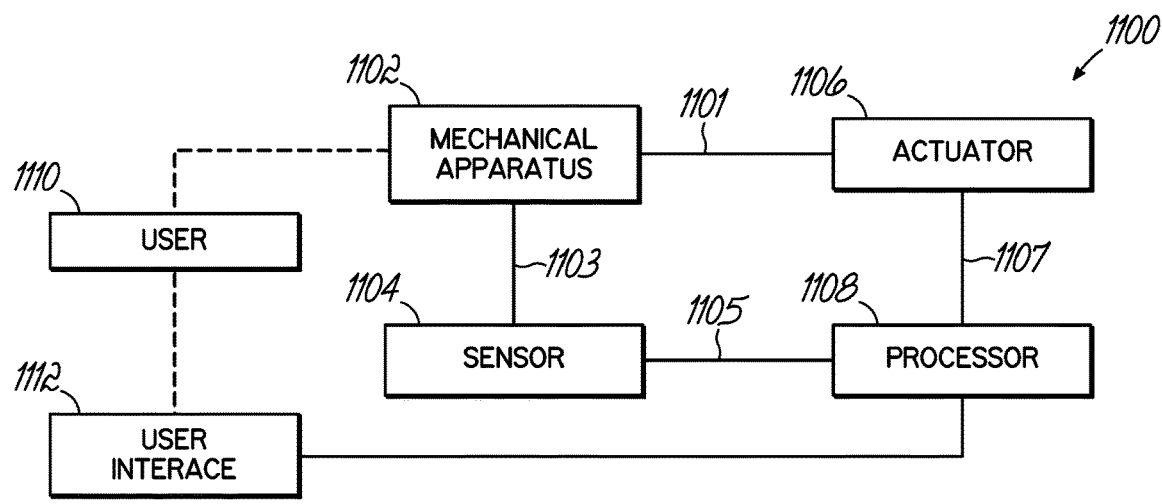
FIG. 8 is a block diagram of a system for performing exercise, according to an embodiment.

FIG. 8 is a block diagram of a system 1100 for performing exercise, according to an embodiment. The example systems described with reference to FIGS. 1A-1D (and many others that would be readily apparent to persons of ordinary skill in the art) are generalized by the schematic system of FIG. 8. According to an embodiment, system 1100 includes a mechanical apparatus 1102 that receives a mechanical exertion from a user, at least one sensor 1104, an actuator 1106, and a processor 1108 interacting with a user 1110 via a user interface 1112. The mechanical apparatus 1102 that receives a mechanical exertion from user 1110 constrains the resulting force and/or displacement of the mechanical apparatus according to a specified force and velocity profile.

The sensor 1104 measures force and displacement of the mechanical apparatus 1102 via a mechanical coupling represented by line 1103. The force and displacement of the apparatus, which is the result of exertion from the user 1110, is measured by sensor 1104, which generates a signal that is provided to the processor 1108 via connection 1105. The processor 1108 communicates with actuator 1106 via line 1107, and provides feedback to the user on user interface 1112, and the actuator mechanically controls the displacement of the mechanical apparatus 1102 (as represented by line 1101) so that the displacement of the apparatus is responsive to the exertion from the user as measured by signals received from the processor 1108 over line 1105. Notably, the processor 1108 receives signals from the sensor 1104 and sends signals to the actuator 1106 to control the actuator 1106 to cause the user to follow the specified force and velocity profile, providing feedback to the user from the signals generated by the sensor 1104. The user interface providing feedback to the user may include a display screen, audio system, headphones, or haptic system. The user interface may also include a touch screen, keypad, pushbuttons, pointing device, microphone, facial recognition or gesture recognition system, or any other known interface through which the user can control or provide parameters to the system.

The processor 1108 performs various operations to control system 1100 in response to received signals and user input as determined by a set of computer program instructions. Such instructions may be stored on a non-transitory computer readable storage device. The computer program instructions specify operations to be performed by the processor 1108. For example, when executed by a processor, the computer program instructions cause the processor to (1) measure a maximum voluntary contraction (MVC) exerted by a user, (2) determine a protocol for the exercise based on the measured MVC, (3) prompt the user to perform the exercise according to the determined protocol, (4) guide the user to perform the exercise according to the protocol via displays or prompts, (5) measure force and/or velocity data associated with the exercise performed by the user, and (6) provide feedback to the user regarding the measured force and/or velocity data while the user is performing the exercise via displays or prompts.

According to an embodiment, the computer program instructions further specify operations that cause the processor to determine the exercise protocol, with the protocol including a specified exertion to be performed by a user, a specified force and velocity profile governing the exertion, and a specified sequence of repetitions of the exertion. The computer program instructions may further specify operations that cause the processor to determine and store on the non-transitory computer readable storage device, one or more of the following pieces of information related to exercise performed by a user: an identity of the user and corresponding MVC for the user, a matrix of muscle group exertions, repetitions, and rest periods based on a percentage of the MVC, a selection of an exercise regimen, data related to an exercise regimen performed by a user regarding a degree to which the user complies with the exercise protocol, and a date and time of an exercise regimen performed by a user along with parameters related to the exercise regimen.

According to an embodiment, further information that may be determined and stored includes at least one of: identification of a type of exercise machine being used (e.g., abdomen (FIGS. 1A and 1D), arm curl (FIG. 1B), leg curl (FIG. 1C), etc.), velocity of exercise (e.g., slow, moderate, fast, etc.), and whether the protocol relates to a fixed or stepped regimen. Further, the processor may be configured (e.g., programmed) to determine a nominated regimen and allow the user to change the default regimen and its parameters to one preferred by the user. As noted above, parameters and preferences set by the user may be transferred to the user's mobile device for later retrieval prior to the commencement of a later exercise session at the same machine.

The MVC measurement position, e.g., the position where maximum force MVC is measured, may also be determined based upon physical parameters of the user, and/or stored data. Such MVC measurement positions may or may not have relevance to other muscle group measurements.

In the event the user measures MVC at a location other than the optimal location for the user's known physical parameters, the control system may compensate the measured MVC based upon a predicted relationship of force and/or leverage of the particular musculo-skeletal system engaged by the exercise vs. position of the apparatus, so that an MVC at the optimal location can be predicted and used for a subsequent exercise.

Parameters related to a range of motion (e.g., start position and end position) may also be determined and stored. The ability to adjust the range of motion is important to accommodate physical characteristics of the user. For example, a tall person may require a larger range of motion relative to a user who is shorter than average. Parameters related to range of motion may also be related to the MVC measurement position.

The computer program instructions may further specify protocols for receiving user input. For example, when executed by a processor, the computer program instructions may control the processor to display a menu of user-selectable options on a display device. The computer program instructions may further cause the processor to receive user selections from a graphical user input device. For example, a person of shorter than average height may require a smaller range of motion relative to an average or tall user. As a further example, the processor may receive information regarding a muscle group to be exercised, a machine ID, etc., which establishes parameters for the particular machine. Parameters may include force levels, ranges of motion, MVC measurement position, etc.

According to an embodiment, a user may initiate an exercise session by interacting with a user input device such as the display device 20. The user may turn the system on by engaging a power switch separate from the user input device, and then initiate an exercise session through providing touch input to a touch screen display device.

FIGS. 1A, 1B, 1C and 1D illustrate a display device that is implemented by the machine, but as noted above the user input device may also be a personal device such as a portable computer, tablet or smart phone equipped with a compatible App, communicating via a communication interface (e.g., 220, FIG. 2).

A user may select a preferred exercise from a displayed menu item. Upon initialization of the system, the processor may identify the exercise machine and provide user options to select. In one example, the user may select a test or exercise mode. The test mode may prompt the user to provide an exertion to the mechanical apparatus so that a MVC may be measured. The test mode may also measure a user's endurance levels. The test mode may be based on predetermined settings such as a MVC measurement position and may implement a compensation in the event that MVC measurement is made at a position that is not optimal based upon the user's physiology.

According to an embodiment, a user selecting an exercise mode may be presented with a menu from which one of an isometric, isokinetic, isotonic, and/or isodynamic exercise may be selected. The system may be configured to present a user with further options including enabling a user to select between a fixed or stepped regimen. According to an embodiment, a fixed regimen is one having the same force profile, repetitions, velocity profile, rest periods, etc., throughout the duration of the exercise session. A stepped regimen may be one in which the system adjusts various parameters (e.g., force profile, repetitions, velocity profile, rest periods, etc.) during the duration of the exercise session. In the stepped regimen, such parameters may be adjusted according to previously determined levels dependent upon a number of steps selected.

According to an embodiment, the isokinetic mode may have a fixed velocity (slow, medium, fast) based on a cycle time and may have a fixed or variable force. Whether the force is fixed or variable may be chosen as a user-selectable option. In one example, the force may have a value based on a percentage of the user-specific measured MVC. According to an embodiment, the isotonic mode may have a fixed (slow, medium, and fast) velocity or variable velocity while the force is maintained at a fixed value. The fixed value of the force may be based on a percentage of the user-specific measured MVC. Whether the velocity is fixed or variable may be chosen as a user-selectable option. When selected, the isodynamic mode may alternate effort repetitions of either isokinetic or isotonic exercise with repetitions of isometric exercise.

According to an embodiment, following selection of exercise mode and parameter selection, the exercise regimen may begin when the user-applied force reaches a predetermined target force level, after which the apparatus moves according to a defined profile as long as the force level is maintained near to the desired target. The user may be prompted to continue applying the target force to the movable mechanical apparatus. In one example, the user may be prompted by a display device that may display a visual indicator of the applied force. In an example embodiment, the visual indicator may be a bar-graph of the applied force. The visual indicator may further indicate the target force level to alert the user to the degree to which the applied force agrees with the predetermined target force. In an example embodiment, the user may move the mechanical apparatus by applying a greater or lesser force so as to keep the displayed bar-graph at the predetermined target level throughout the exercise regimen. In further embodiments, other visual indicators (e.g., an analog dial) may be displayed.

According to an embodiment, an audible alarm may be issued if the target force is exceeded by a predetermined amount. For example, an audible alarm may sound or a visually displayed warning may occur if the applied force exceeds 120% of the predetermined target force levels. In other embodiments, the audible alarm may sound if the applied force exceeds a different predetermined percentage of the target force levels. An audible alert may also sound at the beginning and end of each new portion of the exercise regimen. A score may be computed and displayed during the course of the exercise regimen. The score may characterize a degree to which the user complies with the specified exercise protocol.

In further embodiments, a countdown timer may be displayed to indicate to a user the amount of time (e.g., in seconds, minutes, etc.) remaining during a prescribed exercise protocol or its effort and rest period segments. The exercise protocol may be divided into two or more effort periods. At completion of each effort period, the display may be configured to change from displaying force information to display a visual count-down, or include both in the same display. The countdown may indicate a decreasing time remaining in a rest period. In further embodiments, the countdown may indicate a decreasing time remaining in an effort period. In further embodiments, the display may alternate between displaying the visual countdown with displaying an average score earned during the previous efforts.

During the effort an instantaneous compliance score is displayed in the form, for example, of a percentage of target effort. At the end of all repetitions, the display may show the average score for all efforts periods and may recommend corrective actions when the computed average score has a value that is less than 90% of an expected score (e.g., an expected score may be 100%). In further embodiments, corrective actions may be recommended when the average score have a value less that a different predetermined percentage of the expected score. At the end of an exercise regimen, the system may be configured to automatically shut off when the user ceases to engage the system for a predetermined period of time (e.g., after 5 minutes, after 10 minutes, etc.).

The computer program instructions may further specify operations that cause the processor to record and store various pieces of data on the non-transitory computer readable storage device. Such information may include the date and time during which an exercise regimen is performed. Further information that may be determined and stored includes the exercise type, exercise parameters including a user-specific MVC, and the above-mentioned score associated with the exercise session. Such information may be stored on the non-transitory computer readable storage device or may be downloaded to a personal computer, smart phone, tablet computer, or other computing device.

Embodiments such as those noted above may be implemented using software, hardware, and/or operating system implementations other than those described herein. Any software, hardware, and operating system implementations suitable for performing the functions described herein can be utilized. Embodiments are applicable to both a client and to a server or a combination of both.

Devices made in accordance with the following description may incorporate pneumatic actuation, hydraulic actuation, electrical actuation, and mechanical actuation in different forms of equipment not limited to those portrayed in the figures. Any of these forms of actuation may be used in the implementations shown in FIGS. 1A, 1B, 1C and 1D.

CONCLUSION

The Summary and Abstract sections may set forth one or more but not all example embodiments and thus are not intended to limit the scope of embodiments of the invention and the appended claims in any way.

Embodiments have been described above with the aid of functional building blocks illustrating the implementation of specified functions and relationships thereof. The boundaries of these functional building blocks have been arbitrarily defined herein for the convenience of the description. Alternate boundaries can be defined to the extent that the specified functions and relationships thereof are appropriately performed.

The foregoing description of specific embodiments will so fully reveal the general nature of embodiments of the invention that others can, by applying knowledge of those of ordinary skill in the art, readily modify and/or adapt for various applications such specific embodiments, without undue experimentation, without departing from the general concept of embodiments of the invention. Therefore, such adaptation and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the specification is to be interpreted by persons of ordinary skill in the relevant art in light of the teachings and guidance presented herein.

Generally, the breadth and scope of embodiments of the invention should not be limited by any of the above-described example embodiments, but should be defined only in accordance with the following claims and their equivalents.

What is claimed is:

1. A processor based method of performing an exercise, the method comprising:
measuring, by a processor, a maximum voluntary contraction (MVC) exerted by a large muscle group of a user;
determining a protocol for the exercise based on the measured MVC, wherein the protocol comprises:
a specified exertion to be performed by a user;
a specified force and non-zero velocity profile governing the exertion;
a specified duration for the exertion; and
a specified sequence of repetitions of the exertion and rest periods;
prompting the user to perform the exercise according to the determined protocol;
guiding the user to perform the exercise according to the force and velocity profile;
measuring, via sensor coupled to the processor, force and velocity data associated with the exercise performed by the user;
providing feedback from the processor to the user regarding the measured force and/or velocity data while the user is performing the exercise;
scoring user compliance during the exercise in the processor; and
concluding the protocol.

2. The method of claim 1, further comprising:
determining the specified force and velocity profile based on a predetermined percentage of the MVC.

3. The method of claim 2, further comprising:
determining the protocol comprising a time duration of muscle group exertions that is inversely proportional to the predetermined percentage of MVC.

4. The method of claim 1, further comprising:
determining the specified sequence of repetitions to include a specified rest period, wherein the specified rest period is related to a time duration and level of muscle group exertions.

5. The method of claim 1, further comprising:
determining the specified force and velocity profile governing the exertion to comprise at least one of:
an isokinetic exercise comprising a fixed non-zero velocity and constant or variable force;
an isotonic exercise comprising a constant force with constant or variable non-zero velocity; and
an isodynamic exercise comprising an isokinetic or isotonic exercise combined with an isometric exercise comprising a specified force profile with zero fixed velocity.

6. The method of claim 5, further comprising:
receiving a user selection of an exercise modality from one of:
an isometric exercise;
an isokinetic exercise;
an isotonic exercise; and
an isodynamic exercise;
determining the protocol for the exercise based on the received user selection.

7. The method of claim 1, further comprising:
providing feedback to the user that informs the user of a degree to which the user complies with the exercise protocol during a training effort, comprising one or more of an average compliance score and instantaneous compliance score, delivered during exercise, during rest periods and/or at the conclusion of the exercise protocol.

8. The method of claim 1, further comprising:
determining the protocol to comprise:
a fixed regimen in which the force and velocity profile is the same for each of the repetitions of the exertion; or
a stepped regimen in which the force and/or velocity profile varies over a plurality of repetitions within the sequence of repetitions of the exertion.

9. The method of claim 1, further comprising:
determining two or more user selectable exercise regimens;
receiving a user selection of an exercise regimen; and
determining the protocol based on the user selection.

10. The method of claim 1 further comprising obtaining physical dimensions of a user and computing therefrom a range of motion for the user, and incorporating the range of motion in the protocol for the exercise.

11. The method of claim 10 wherein the step of measuring a maximum voluntary contraction is performed at an optimal position in the computed range of motion for the user.

12. The method of claim 10 wherein the step of measuring a maximum voluntary contraction is performed at a first position in the computed range of motion for the user, and the method further comprises computing a maximum voluntary contraction at an optimal position in the computed range of motion for the user based upon a predicted relationship of force and leverage of the musculo-skeletal system of the user.

13. The method of claim 1 further comprising
connecting a mobile computing device to the processor,
storing at least a portion of the protocol in the mobile computing device, and
retrieving at least a portion of the protocol from the mobile computing device.

14. The method of claim 1 further comprising
connecting a mobile computing device to the processor, and
providing the feedback from the processor to the user via a display screen of the mobile computing device.

15. The method of claim 1 further comprising
connecting a mobile computing device to the sensor,
wherein the processor is incorporated into the mobile computing device.

16. A system for performing exercise, the system comprising:
a mechanical apparatus that receives a mechanical exertion from a user and constrains the resulting force and displacement of the mechanical apparatus according to a specified force and velocity profile;
a sensor that measures force and displacement of the mechanical apparatus resulting from the exertion from the user;

an actuator that controls the displacement of the mechanical apparatus in response to the exertion from the user; and a processor that receives signals from the sensor and sends signals to the actuator, wherein the processor is configured to perform the following operations:

measuring a maximum voluntary contraction (MVC) exerted by a user based on a signal received from the sensor in response to the exertion;

determining a protocol for the exercise based on the measured MVC, wherein the protocol comprises:
a specified exertion to be performed by a user;
a specified force and non-zero velocity profile governing the exertion; and
a specified sequence of repetitions of the exertion spaced by rest periods;

prompting the user to perform the exercise according to the determined protocol;

sending signals to the actuator to constrain the user to perform the exercise according to the force and velocity profile;

measuring force and/or velocity data associated with the exercise performed by the user based on signals received from the sensor;

providing feedback to the user, while the user is performing the exercise, regarding the measured force and/or velocity data based on signals received from the sensor; and providing one or more compliance scores to the user during the exercise, during rest periods and/or at the conclusion of the protocol.

17. The system of claim 16, wherein the processor is further configured to:
determine the specified force and velocity profile based on a predetermined percentage of the MVC.

18. The system of claim 17, wherein the processor is further configured to:
determine the protocol to comprise a time duration of muscle group exertions that is inversely proportional to the predetermined percentage of MVC.

19. The system of claim 17, wherein the processor is further configured to:
determine the specified sequence of repetitions to include a specified rest period, wherein the specified rest period comprises a time duration that is related to a time duration of muscle group exertions.

20. The system of claim 19, wherein the processor is further configured to:
determine the specified force and velocity profile governing the exertion to comprise at least one of:
an isokinetic exercise comprising a fixed non-zero velocity and constant or variable force;
an isotonic exercise comprising a constant force with constant or variable non-zero velocity; and
an isodynamic exercise comprising an isokinetic or isotonic exercise combined with an isometric exercise comprising a specified force profile with zero fixed velocity.

21. The system of claim 20, wherein the processor is further configured to:
receive a user selection of an exercise modality from one of:
an isometric exercise;
an isokinetic exercise;
an isotonic exercise; and
an isodynamic exercise; and determine the protocol for the exercise based on the received user selection.

22. The system of claim 16, wherein the processor is further configured to:
provide feedback to the user that informs the user of a degree to which the user complies with the exercise protocol.

23. The system of claim 16, wherein the processor is further configured to:
determine the protocol to comprise:
a fixed regimen in which the force and velocity profile is the same for each of the repetitions of the exertion; or
a stepped regimen in which the force and/or velocity profile varies over a plurality of repetitions within the sequence of repetitions of the exertion.

24. The system of claim 16, wherein the processor is further configured to:
determine two or more user selectable exercise regimens;
receive a user selection of an exercise regimen; and
determine the protocol based on the user selection.

25. The system of claim 16, further comprising a non-transitory computer readable storage device, wherein the processor is further configured to determine and store on the non-transitory computer readable storage device, one or more of the following pieces of information related to exercise performed by a user:
an identity of the user and corresponding MVC for the user;
a matrix of muscle group exertions, repetitions, and rest periods based on a percentage of the MVC;
a selection of an exercise regimen;
data related to an exercise regimen performed by a user regarding a degree to which the user complies with the exercise protocol; and
a date and time of an exercise regimen performed by a user along with parameters related to the exercise regimen.

26. The system of claim 16 further comprising obtaining physical dimensions of a user and computing therefrom a range of motion for the user, and incorporating the range of motion in the protocol for the exercise.

27. The system of claim 26 wherein the step of measuring a maximum voluntary contraction is performed at an optimal position in the computed range of motion for the user.

28. The system of claim 26 wherein the step of measuring a maximum voluntary contraction is performed at a first position in the computed range of motion for the user, and the method further comprises computing a maximum voluntary contraction at an optimal position in the computed range of motion for the user based upon a predicted relationship of force and leverage of the musculo-skeletal system of the user.

29. The system of claim 16 further comprising
connecting a mobile computing device to the processor,
storing at least a portion of the protocol in the mobile computing device, and
retrieving at least a portion of the protocol from the mobile computing device.

30. The system of claim 16 further comprising
connecting a mobile computing device to the processor, and
providing the feedback from the processor to the user via a display screen of the mobile computing device.

31. The system of claim 16 further comprising
connecting a mobile computing device to the sensor, wherein the processor is incorporated into the mobile computing device.

32. A non-transitory computer readable storage device having computer program instructions stored thereon that, when executed by a processor, cause the processor to perform the following operations:
  measuring a maximum voluntary contraction (MVC) exerted by a user;
  determining a protocol for the exercise based on the measured MVC, wherein the protocol comprises:
    a specified exertion to be performed by a user;
    a specified force and non-zero velocity profile governing the exertion; and
    a specified sequence of repetitions of the exertion;
  prompting the user to perform the exercise according to the determined protocol;
  constraining the user to perform the exercise according to the force and/or velocity profile;
  measuring force and velocity data associated with the exercise performed by the user; and
  providing feedback to the user regarding the measured force and velocity data while the user is performing the exercise.

\* \* \* \* \*